US00PP31465P2

(12) United States Plant Patent
Hansen

(10) Patent No.: US PP31,465 P2
(45) Date of Patent: Feb. 18, 2020

(54) ***CAMPANULA* PLANT NAMED 'ANGEL BELLS'**

(50) Latin Name: ***Campanula glomerata* L.**
Varietal Denomination: Angel Bells

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,528

(22) Filed: Nov. 28, 2018

(51) Int. Cl.
*A01H 6/26* (2018.01)
*A01H 5/02* (2018.01)

(52) U.S. Cl.
USPC ..... Plt./414

(58) Field of Classification Search
USPC ..... Plt./414
CPC ..... A01H 5/02; A01H 6/26
See application file for complete search history.

(56) References Cited

PUBLICATIONS http://www.lifeinplants.com/life-in-plants/campanulas-going-once-going-twice-going-three-times. 2015.*
https://perfectplants.co.uk/plants-bulbs/campanula-punctata-wedding-bells-in-a-17cm-pot-ground-cover-plant.html 2015.*

* cited by examiner

*Primary Examiner* — Annette H Para

(57) ABSTRACT

The new and distinct Bellflower plant, *Campanula* plant named 'Angel Bells' with dense, compact, mounded, upright habit; dark-green lanceolate foliage and numerous white campanulate flowers over a seven week period clustered at nodes and ends of on upright stems beginning in late June.

1 Drawing Sheet

Botanical designation: *Campanula glomerata* L.
Cultivar denomination: 'Angel Bells'.

STATEMENT REGARDING PRIOR DISCLOSURES UNDER 37 CFR 1.77(B)(6)

The first public disclosure of the claimed plant was made by Walters Gardens, Inc. on Nov. 28, 2017 when the claimed plant was displayed as a photograph without description in a calendar distributed to customers of Walters Gardens, Inc., who obtained the plant and all information relating thereto, from the inventor. No plants of *Campanula* 'Angel Bells' have been sold, in this country or anywhere in the world as of the filing date of this application, nor has any disclosure of the new plant been made, more than one year prior the filing date of this application, and such disclosure within one year was either derived directly or indirectly from the inventor.

BACKGROUND OF THE PLANT

The present invention relates to the new and distinct clustered bellflower herein also referred to as *Campanula* 'Angel Bells', by the cultivar name, 'Angel Bells', or as the new plant. The new plant was derived from seed collected on Oct. 8, 2014 from a plant in an isolation block, in a research facility in Zeeland, Mich., that was an unreleased, proprietary, selection identified by the breeder code "Lavender". The specific male parent was a sibling of "Lavender". The single seedling represented by 'Angel Bells' was selected from a group of seedlings by the inventor, isolated and compared in subsequent years to other *Campanula* and subsequently found to be different from all cultivars known to the discoverer and eventually given the breeder code 14-1-7.

Asexual propagation at the same nursery in Zeeland, Mich., USA by basal cuttings has shown 'Angel Bells' to be stable and reproduce true to type in successive generations since late June 2016.

SUMMARY OF THE PLANT

*Campanula* 'Angel Bells' has not been observed in all possible environmental conditions. The phenotype may vary slightly with changes in environments such as light intensity, fertility, water availability, etc. without, however any variation in genotype.

*Campanula* 'Angel Bells' is distinct from all cultivars known to the inventor in the following traits:

1. Narrow serrate foliage with compact height and dense mounded habit.
2. Heavily-branched with white bell-shaped flowers clustered at the nodes and ends of upright stems.
3. Dark green foliage.
4. Long flowering period beginning with concentration in late-June and continuing for about 7 weeks.

Plants of *Campanula* 'Angel Bells' are most similar to 'Allgentiw' U.S. Plant Pat. No. 24,686, 'Allgentiw' is shorter in habit and produces fewer flowers over a shorter period of time. "Lavender" has lavender purple flowers.

BRIEF DESCRIPTION OF THE DRAWINGS

The color drawings illustrate the overall characteristics of *Campanula* 'Angel Bells' as a four-year-old plant. The colors are as true as reasonably possible given the technology available. The color values may vary slightly depending on light intensity and quality.

DETAILED BOTANICAL DESCRIPTION

Figure 1:
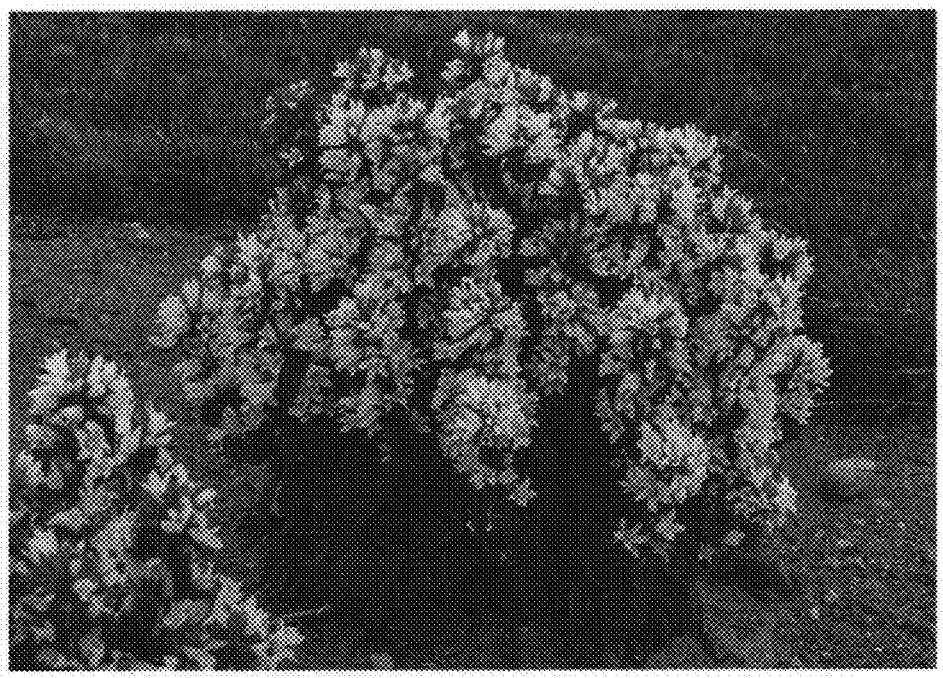
FIG. 1 shows the new plant in a landscape environment.
Figure 2:
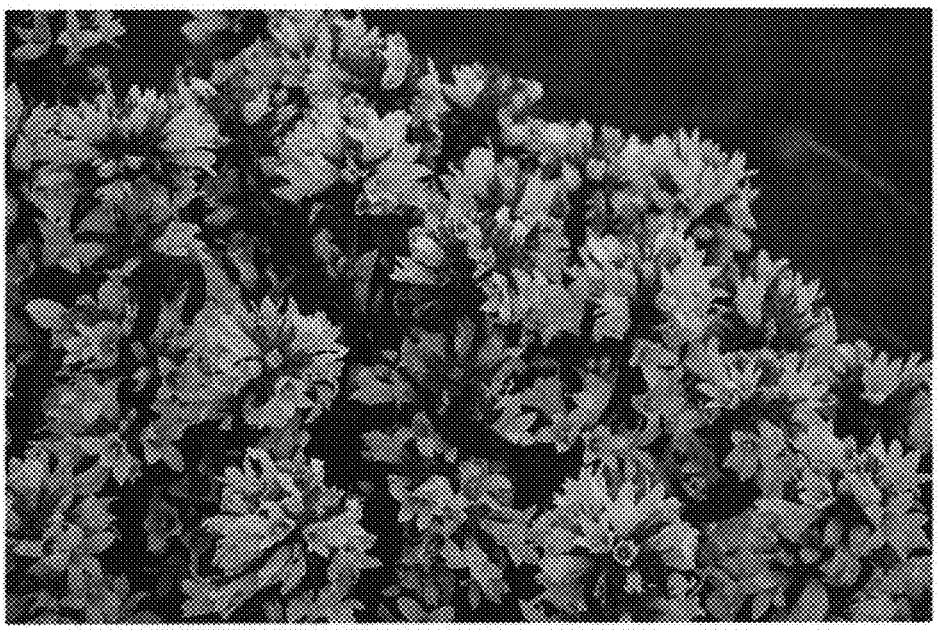
FIG. 2 shows a close-up of the flowers of the new plant.

The following description is based on a four-year-old plant growing in a full-sun trial garden in Zeeland, Mich., USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent "Lavender"; male or pollen parent sibling to "Lavender";

Asexual propagation: Cuttings, about 12 to 20 days to initiate roots; time to finish in a one- gallon container about 9 months;

Plant habit: Up-right, rounded, herbaceous, winter-hardy, perennial mound; with heavily branched flower stems up to 60.0 cm wide and 48.0 cm tall; average about 55.0 cm across and about 45.0 cm tall;

Leaves: Acaulescent and cauline opposite; simple; lanceolate; adaxial surface sparsely, strigillose, slightly lustrous; abaxial surface matte, puberulent; acute apex; cordate to rounded base; margin serrate and ciliolate; up to 16.0 cm long and 4.5 cm wide, average about 14.8 cm long and 8.2 cm wide;

Leaf color: Young expanding leaves adaxial nearest RHS 143B and abaxial between RHS 138B and RHS 138C; mature leaves adaxial between RHS NN137A and RHS 139A, abaxial nearest RHS 148C;

Veins: Reticulate;

Vein color: Adaxial midrib and main veins nearest RHS 145C and secondary veins nearest RHS 137C, abaxial midrib and main veins nearest RHS 146D and secondary veins nearest RHS 146A;

Stem color: Blend between RHS 145A and RHS N144A between carina, and carina nearest NN137C;

Flower: Single; perfect; campanulate; on terminal branches; about 22.0 mm across, about 20.0 mm tall; attitude outright to slightly upright;

Inflorescence fragrance: Not detected;

Calyx: Campanulate; to about 24.0 mm wide and 7.0 mm wide at base;

Sepals: Five; lanceolate; acute apex; fused in the basal 2.0 mm; margin serrulate and ciliolate; glabrous adaxial; puberulent adaxial; about 5.0 mm long and about 1.5 mm wide above fusion;

Sepal color: Abaxial and adaxial nearest RHS 146D;

Flowering period: Beginning early summer, for about 7 weeks; producing over 100 flowers per branched stem and over 500 flowers per plant at one time during peak flowering;

Flower longevity: 5 to 7 days;

Flower buds: One day prior to opening — oblong, rounded apiculate apex, about 14.0 mm long and 4.0 mm diameter; four days prior to opening — about 8.0 mm long and 3.5 mm diameter near apex;

Flower bud color: One day prior to opening — nearest RHS NN155A; four days prior to opening — nearest RHS 1D;

Peduncle: About 12 per plant; cylindrical, carinate with longitudinal angular ridges along sides of leaf attachment; glabrous; glaucous; upright attitude; strong; heavily-branched; about 6.0 mm diameter at base and 42.0 cm long; about nine nodes, average internode spacing about 4.6 cm; branches to about 14.0 cm long and 3.5 mm diameter at base;

Peduncle color: Blend between RHS 145A and RHS N144A between carina, and carina nearest NN137C;

Pedicel: Cylindrical; glaucous; thin, wiry, strong; average about 2.0 mm long and 0.5 mm diameter;

Pedicel color: Lighter than RHS 146D;

Petals: Typically five in single whorl; lanceolate; acute apex; basal 14.0 mm fused; pubescent adaxial and glabrous abaxial; about 22.0 mm long and 5.0 mm wide above fusion;

Petal color (primary and secondary): Adaxial nearest RHS NN155D; abaxial nearest RHS NN155D with midrib nearest RHS 155C; no spots are present either adaxial or abaxial; no change in flower color from opening to maturity;

Corolla: Single; to about 18.0 mm long and 20.0 mm across; fused in basal 14.0 mm; fused portion to about 10.0 mm diameter distally and 4.0 mm diameter at base; lobes slightly reflexed to produce nearly flat face; corolla lobe apices acute;

Androecium: Typically five;

*Filament*.—About 2.0 mm long and 0.3 mm diameter; color nearest RHS NN155D.

*Anther*.—Lanceolate; about 5.0 mm long and 1.5 mm across; color nearest RHS 13B.

*Pollen*.—Not abundant; color nearest RHS 4D.

Gynoecium: Single; about 20.0 mm long;

*Style*.—Cylindrical; about 18.0 mm long and 0.5 mm diameter; color nearest RHS 13B.

*Stigma*.—Trifid; recurved; about 3.0 mm long and 0.5 mm diameter; color nearest RHS 8D.

Seed: Slightly flattened ellipsoidal; rounded apex and base; surface glabrous; about 1.0 mm long and 0.7 mm across center;

Seed color: Variable, some seeds between RHS 165A and RHS 165B;

*Campanula* 'Angel Bells' is tolerant of winter temperatures from USDA hardiness at least to zones 4 to 8. The new plant grows best with good drainage and adequate moisture. It is not known to be tolerant of diseases and pest that are common to other *Campanula* cultivars.

I claim:

1. The new and distinct cultivar of *Campanula* plant named 'Angel Bells' as described and illustrated.

* * * * *